United States Patent [19]

Bowman

[11] Patent Number: 4,845,253

[45] Date of Patent: Jul. 4, 1989

[54] SILVER-BASED CATALYST FOR VAPOR PHASE OXIDATION OF OLEFINS TO EPOXIDES

[75] Inventor: Robert G. Bowman, Midland, Mich.

[73] Assignee: The Dow Chemical Company, Midland, Mich.

[21] Appl. No.: 124,133

[22] Filed: Nov. 23, 1987

[51] Int. Cl.$^4$ ............................................. C07D 301/10
[52] U.S. Cl. .................... 549/536; 502/243; 549/524; 549/537
[58] Field of Search ............... 549/523, 536; 502/243, 502/524, 537

[56] References Cited

U.S. PATENT DOCUMENTS

| | | | |
|---|---|---|---|
| 3,585,217 | 6/1971 | Titzenthaler | 260/348.5 |
| 3,888,889 | 6/1975 | Kolombus et al. | 549/536 |
| 3,899,445 | 8/1975 | Kajimoto et al. | 549/536 |
| 3,959,316 | 5/1976 | Piccinini et al. | 549/536 |
| 4,007,135 | 2/1977 | Hayden et al. | 549/536 |
| 4,272,443 | 6/1981 | Titzenthaler et al. | 549/536 |
| 4,305,844 | 12/1981 | Vangermain et al. | 502/243 |

FOREIGN PATENT DOCUMENTS

| | | | |
|---|---|---|---|
| 2933950 | 3/1981 | Fed. Rep. of Germany | 502/243 |
| 53-39404 | 10/1978 | Japan | 502/243 |

OTHER PUBLICATIONS

W. M. H. Sachtler et al., Catal. Rev.–Sci. Eng., 23, (1 & 2), 127–149, (1981).

Primary Examiner—Asok Pal
Attorney, Agent, or Firm—Marie F. Zuckerman

[57] ABSTRACT

A process of oxidizing an olefin having at least three carbon atoms directly to the corresponding epoxide comprising contacting the olefin with oxygen in the presence of a catalyst comprising a mixed silver-promoter metal (+2 or +3) silicate. In the direct oxidation of propylene the process yields a high selectivity to propylene oxide.

20 Claims, No Drawings

SILVER-BASED CATALYST FOR VAPOR PHASE OXIDATION OF OLEFINS TO EPOXIDES

BACKGROUND OF THE INVENTION

This invention relates to a catalyst and process for the direct oxidation of olefins to epoxides by molecular oxygen.

The direct oxidation of olefins to epoxides by molecular oxygen is well-known. The usual catalyst contains metallic or ionic silver, optionally modified with promoters and activators, such as alkaline earth metals or metal salts. U.S. Pat. No. 4,007,135, for example, lists many promoters, including calcium, magnesium, strontium, cadmium, and copper. Most of the catalysts contain a porous, inert support or carrier, upon which the silver and promoter are deposited. A review of the direct oxidation of ethylene in the presence of such silver catalysts is given by W. M. H. Sachtler, C. Backx, and R. A. Van Santen in *Catalysis Reviews: Science and Engineering*, 23 (1&2), 127-149 (1981).

Some patents of the prior art teach the use of catalysts containing silver and silicon in the direct oxidation of olefins. Specifically, U.S. Pat. No. 3,585,217 teaches a catalyst of silver silicate, optionally containing activator compounds, for use in the epoxidation of ethylene. This catalyst is disclosed to have a low activity. U.S. Pat. No. 4,272,443 teaches a catalyst comprising a support coated with lithium silicates and silver salts, such as silver silicate, for the epoxidation of ethylene. Japanese Koho 1978 - 39,404 (Oda) teaches a catalyst containing predominately elemental silver, and lesser amounts of cadmium and silicon oxides for the epoxidation of propylene.

It is well-known that most catalysts for the direct oxidation of ethylene to ethylene oxide do not give comparable results in the corresponding oxidation of the higher olefins, such as propylene. It would be desirable to have a catalyst for the direct oxidation of olefins which achieves a high selectivity for olefin oxides, particularly the higher olefin oxides. It would be even more desirable if such a catalyst were to possess a high level of activity.

SUMMARY OF THE INVENTION

The invention is the process of epoxidizing higher olefins comprising contacting at least one higher olefin with oxygen in the presence of a catalyst under conditions sufficient to produce the corresponding olefin oxide. For the purposes of this invention a higher olefin is defined as an olefin containing at least three carbon atoms. The catalyst is prepared by a process comprising contacting in an aqueous solution the following dissolved salts:

(a) a silver-containing salt:
(b) at least one salt containing a multivalent cation promoter: and
(c) a silicon-containing salt, wherein the mole ratio of silicon to combined silver and promote metals is at least about 0.5, under conditions sufficient to form a mixed silver-promoter silicate precipitate. This catalyst when tested in the epoxidation of propylene, as described hereinafter, produces a conversion of propylene greater than about 0.20 mole percent and a selectivity to propylene oxide greater than about 28 mole percent.

It is surprising that the precipitation of a mixed silver-promoter silicate from a solution containing a mole ratio of silicon to combined silver and promoter metals of at least about 0.5 would produce a catalyst with improved activity and selectivity in the epoxidation of the higher olefins to their corresponding olefin oxides. The epoxides formed from olefins pursuant to this invention are well-known, and are particularly useful for the production of polyether polyols.

DETAILED DESCRIPTION OF THE INVENTION

The silver-containing salt can be any silver salt which is water-soluble and which will not adversely react with the silicate-containing salt to form an undesirable precipitate. Pertaining to the silver-containing salt, the term "water-soluble" means a solubility of at least about 1.0 g silver salt per liter water. An undesirable precipitate is defined as one which interferes with the formation of the mixed silver-promoter silicate catalyst, or contaminates the mixed silver-promoter silicate catalyst. An undesirable precipitate will occur, for example, if the anion of the silver-containing salt reacts with the cation of the silicate-containing salt to yield an insoluble solid. Examples of suitable silver-containing salts include silver benzoate, silver chlorate, silver perchlorate, silver chlorite, silver fluogallate, silver fluoride, silver fluorosilicate, silver nitrate, silver nitrite, silver propionate and silver sulfate: but the silver-containing salt is not meant to be limited to only these examples. Preferred are silver chlorate, silver perchlorate, silver fluoride and silver nitrate. Most preferred is silver nitrate.

The promoter-containing salt may be any multivalent cation salt which is water-soluble and which will not adversely react with the silicate salt to form an undesirable precipitate. Pertaining to the promoter-containing salt, the term "water-soluble" means a solubility of at least about 0.05 g promoter salt per liter water. An undesirable precipitate is defined hereinbefore, and may be formed if the cation of the silicate-containing salt reacts with the anion of the promoter-containing salt. Promoter-containing salts which form precipitates with the silver-containing salt may be used, on condition that the precipitate is removed prior to addition of the silicate solution. After removal of said precipitate the amount of silver remaining in solution may have to be adjusted to replace any silver which may have been lost. Preferably, the promoter salts are water-soluble salts having dipositive or tripositive cations selected from the group consisting of Group IIA, Group VIII, Group IB (excluding silver), Group IIB, and the rare earth lanthanide (atomic weights 57–71) metals. More preferably, the promoter salts are water-soluble nitrate, chlorate, perchlorate, and fuuoride salts having dipositive or tripositive cations selected from the group of metals consisting of beryllium, magnesium, calcium, strontium, barium, cobalt, nickel, copper, zinc, cadmium, praseodymium, neodymium, europium, gadolinium, holmium, and lutetium. Most preferably, the promoter salts are water-soluble nitrates having dipositive or tripositive cations selected from the group of metals consisting of beryllium, magnesium, calcium, strontium, barium, cobalt, nickel, copper, zinc, cadmium, praseodymium, neodymium, europium, gadolinium, holmium, and lutetium. Examples of suitable promoter salts are the following: beryllium fluoride, calcium nitrate, cadmium potassium sulfate, cobalt (II) chlorate, copper (II) nitrate, europium nitrate, nickel hypophosphite, magnesium nitrate, praseodymium (III) nitrate, and zinc borate. However, the promoter-containing salts are not limited thereto.

The silicate-containing salt can be any silicate salt which is water-soluble and which will not adversely react with the silver-containing and promoter-containing salts to form an undesirable precipitate, as defined hereinbefore. More specifically, if the cation of the silicate-containing salt reacts with the anion of either the silver-containing salt or a promoter-containing salt, an undesirable precipitate may form. Pertaining to the silicate-containing salt, the term "water-soluble" means a solubility of at least about 1.0 g silicate salt per liter water. Examples of suitable silicate-containing salts are sodium silicate, ammonium silicate, sodium disilicate, sodium metasilicate, sodium orthosilicate, potassium metasilicate and potassium tetrasilicate; however, the silicate-containing salt is not meant to be limited thereto. Preferred are the Group IA metal silicate salts. More preferred are sodium silicate, sodium disilicate, sodium metasilicate and sodium orthosilicate. It is noted that when any one of the above-identified silicate salts is dissolved in water, a distribution of silicate species is present in the solution. The distribution will depend upon the pH of the solution. Thus, for example, if an aqueous solution of sodium disilicate is prepared, the solution will contain predominately $Si_2O_5^{-2}$ anions, and lesser amounts of $SiO_3^{-2}$ and $Si_3O_7^{-2}$ ions, plus other oligomeric species.

In accordance with the practice of the invention, the catalyst is prepared from an aqueous solution containing a silver-containing salt, a silicate-containing salt, and at least one salt containing a multivalent cation promoter. The mole ratio of silicon to combined silver and promoter metals may be any that gives rise to the mixed silver-promoter silicate precipitate having the catalytic properties described hereinafter. Preferably, the mole ratio of silicon to combined silver and promoter metals is at least about 0.50:1. More preferably, the mole ratio of silicon to combined silver and promoter metals is greater than about 0.60:1, more preferably greater than about 0.70:1: preferably less than about 10.0:1, more preferably less than about 3.5:1. The number of moles of silicon is based on the water-soluble silicate-containing salt, and does not include the silicon arising from any silica support which may be employed. The mole ratio of silver to multivalent cation promoter may be any that gives rise to the mixed silver-promoter silicate precipitate having the catalytic properties described hereinafter. Preferably, the mole ratio of silver to promoter is at least about 1.0:1. More preferably, the mole ratio of silver to promoter is greater than about 1.4:1, most preferably greater than about 2.0:1: more preferably less than about 100:1, most preferably less than about 20:1. The number of moles of promoter are taken as the combined moles of all cation promoters in solution and does not include cations associated with any support which may be employed.

The preparation of the catalyst from the silver, promoter, and silicate-containing salts is a relatively simple procedure. Two aqueous solutions are prepared. The silicate-containing salt is mixed with sufficient water to dissolve the salt in a container, such as a glass flask or beaker, to form a first water solution. The mixing can be at room temperature and open to the atmosphere. The silver-containing salt and all of the promoter-containing salts are mixed with sufficient water to dissolve the salts in a container, such as a glass flask or beaker, to form a second water solution. The mixing can also be at room temperature, or alternatively at elevated temperatures, and open to the atmosphere.

The two water solutions, described hereinabove, are contacted to form a third water solution containing the following dissolved salts: a silver-containing salt, a silicate-containing salt and at least one salt containing a promoter. The first water solution and the second water solution can be contacted in any effective manner such as flowing the two water solutions into a container such as a laboratory flask or beaker, adding the second water solution to the first water solution, or adding the first water solution to the second water solution. Preferably, the resulting mixture of the first and second water solutions is stirred during this contacting step. Most preferably the first water solution (containing the silicate-containing salt) is added with mixing to the second water solution (containing the silver-containing salt and all of the promoter-containing salts). The mixing of the first and second water solutions is carried out at room temperature and opened to the atmosphere.

A solid precipitates from the third water solution. The solid precipitate is filtered from its mother liquor. The resulting filter cake is broken into smaller particles by conventional methods, such as by jabbing with a glass stirring rod. The particles are washed by suspending the particles in water, stirring, and then refiltering the suspended particles. The washing is repeated about three times. The washed particles are dried, such as by drying in air at 150° C. overnight, to produce the catalyst.

When the two water solutions are contacted in the most preferred manner as described hereinabove, the silver ions and promoter ions precipitate essentially simultaneously as a composition comprising a mixed silver-promoter silicate. As noted hereinbefore, the silicate is actually a distribution of silicate anions. The following theory is proposed to account for the improved activity of the mixed silver-promoter silicate catalyst; however, the scope of the invention should not be limited or bound to such a theory. It is believed that when the silver ions and promoter ions are precipitated simultaneously, the silver ions and promoter ions occupy nearest neighbor cation positions in the mixed silicate salts. In such a composition the silver ions and the promoter ions are in close proximity to each other. This composition contrasts with that in which a discrete silver silicate salt is physically mixed with a discrete promoter compound of any type, for example, in the case where the silver ions and promoter ions are deposited sequentially. It is believed that in such physical mixtures the nearest neighbor cation positions are occupied by ions of the same species, that is, silver next to silver and promoter next to promoter, with some minor exception at the edges where the two salts contact. As will be seen in the Examples hereinafter, a catalyst prepared by the most preferred method of this invention and comprising the mixed silver-promoter silicate exhibits advantageous properties in the epoxidation of olefins.

The mixed silver-promoter silicate catalyst may be used as is, or may be used supported on an inert carrier. Any refractory oxide which does not interfere with the oxidation reaction will provide a suitable support. Examples of such suitable supports are alumina, silica, titania, alkaline earth oxides, rare earth oxides, and mixtures of the above. Alkaline earth carbonates also make suitable supports. Preferably, the support is a refractory oxide. More preferably, the support is silica. Most preferably, the support is Cab-O-Sil ® M-5 fumed silica from Cabot Corporation.

The catalyst of this invention may be activated in situ—in the olefin oxidation reaction, or optionally, activated prior to use. The activation comprises reducing the catalyst with an appropriate reducing agent. If the catalyst is activated in situ, the olefin itself, preferably propylene, is the reducing agent. If the catalyst is activated prior to use, the reduction is carried out by conventional methods, such as by heating overnight at about 150° C. under one atmosphere of from about 1 mole percent to about 10 mole percent hydrogen in nitrogen. If desired, more hydrogen—up to 100 mole percent—may be used. By either method, the reduction produces silver metal and promoter metal in intimate contact with the mixed silver-promoter silicate salt. Typically, from about 70 to about 80 mole percent of the silver is reduced; whereas, the amount of reduced promoter depends on the reduction potential of the promoter and the reducing conditions. Typically, the promoter is not significantly reduced.

The activity of the catalyst of the invention may be tested in the epoxidation of propylene. To measure the performance, the following test can be constructed: The catalyst (10 g) is placed in a $\frac{3}{8}$-inch (9.5 mm) inner diameter, stainless steel reactor, such that a reaction zone of about 3 to about 4 inches in length is created. Glass wool plugs are placed on either end of the reactor to retain the catalyst. A premixed feed is prepared consisting essentially of about 70 volume percent propylene and 30 volume percent oxygen. The feed is passed through a water saturator which saturates the feed with about 3 volume percent water vapor. The water-saturated feed is preheated to the temperature of the reactor. The catalyst is then "burned in" by passing the premixed, preheated feed through the catalyst until the selectivity to propylene oxide stabilizes (typically about 5 days). The "burn in" is conducted at a temperature in the range from about 150° C. to about 180° C., a pressure in the range from about 15 psia to about 250 psia, and a flow rate in the range from about 10 cc/min to about 300 cc/min. The conversion of propylene, selectivity to propylene oxide and specific epoxidation rate are calculated from a gas phase chromatographic analysis of the product stream. Preferably, a catalyst of this invention produces simultaneously a conversion of propylene greater than about 0.2 mole percent, a selectivity to propylene oxide greater than about 28 mole percent, and a specific epoxidation rate at least about 0.8 gram of propylene oxide per kilogram of silver per hour.

The catalyst compositions of this invention typically have surface areas between about 0.1 $m^2/g$ and about 200 $m^2/g$. Preferably the surface area of the catalyst is greater than about 10 $m^2/g$, more preferably greater than about 50 $m^2/g$, most preferably greater than about 70 $m^2/g$. Preferably the surface area of the catalyst is less than about 180 $m^2/g$, more preferably less than about 150 $m^2/g$, most preferably less than about 120 $m^2/g$.

The catalyst compositions of this invention may be used in the direct oxidation of olefins by oxygen to yield the corresponding olefin oxides. Such a process comprises contacting the olefin with oxygen in the presence of the catalyst composition, described hereinbefore, under conditions such that the olefin oxide is formed.

The olefins employed in the process of this invention are any higher olefins which are readily oxidized to epoxides in the presence of silver catalysts. A higher olefin is defined for the purposes of this invention as an olefin containing at least three carbon atoms. Examples of such olefins are propylene, 1-butene, 2-butene, 1-pentene, 2-pentene, styrene, and cyclohexene; however, the process is not limited solely to these examples. Preferably, the olefin is propylene. The olefin is preferably saturated with water vapor. This can be accomplished by bubbling the olefin through liquid water. Small amounts of a usual inhibitor, for example 0.001 to 5 ppm of 1,2-dichloroethane, may be used when the olefin is ethylene.

The oxygen employed in the process of this invention may be obtained from any gas containing molecular oxygen, such as air. The olefin and oxygen are present in an amount sufficient to allow formation of the epoxide of the olefin. Preferably, the oxygen to olefin mole ratio is above about 0.01:1, more preferably above about 0.05:1: the ratio is preferably below about 2:1, more preferably below about 0.40:1.

The reactants can be contacted with the catalyst in any suitable reactor. An example of a suitable reactor is the test reactor described hereinbefore. Preferred are tubular stainless steel reactors designed to withstand the pressure of the reaction. Typically plugs of glass wool are used to keep the catalyst in the reactor. While the contact of the olefin with oxygen and the catalyst can take place in either the vapor phase or in a liquid solvent, contact in the vapor phase is preferred. The feed is preferably preheated to a temperature about that of the reaction temperature.

The pressure and temperature should be adjusted to achieve optimal results for each catalyst and feed mixture. The pressure may be subatmospheric through superatmospheric with superatmospheric pressures preferred. It is more preferred to use a pressure from about 7 psia to about 300 psia. It is even more preferable to use a pressure from about 15 psia to about 100 psia.

The reaction can occur at any operable temperature upon contacting the catalyst and the reactants. Preferred is contact with a catalyst heated to a temperature above about 50° C., more preferred is contact with a catalyst heated to a temperature above about 100° C., and most preferred is contact with a catalyst heated to a temperature above about 140° C. Preferred is contact with a catalyst heated to a temperature below about 300° C., more preferred below about 250° C., most preferred below about 200° C.

The residence time of the reactants in the catalyst zone of the reactor is sufficient to allow for some epoxide formation. In general, the residence time will vary as a function of the scale of the reactor, the quantity of catalyst in the reactor, and the type of reactor. The residence time necessary to promote the desired epoxidation reaction is obtained by controlling the gas hourly space velocity of the reactants passing through the reaction zone. The gas hourly space velocity is expressed in units of volume of gas flow per hour per volume of reactor, or simply $hr^-$, at a specified temperature and pressure. One can readily adjust the gas hourly space velocity to obtain the optimum reaction or contact time. For most reactors a space velocity in the range from about 10 $hr^{-1}$ to about 15,000 $hr^{-1}$ measured at reaction conditions can be employed. Preferably, the space velocity is in the range from about 10 $hr^{-1}$ to about 6000 $hr^-$. More preferably, the space velocity is in the range from about 50 $hr^{-1}$ to about 3000 $hr^-$.

The reaction products are the epoxide of the olefin reactant, carbon dioxide, and water. The epoxides are useful intermediates, particularly useful in the manufacture of urethane polymers.

For the purposes of this invention, the term "conversion" is taken to mean the mole percent of olefin lost from the feed stream as a result of reaction. Likewise, the term "selectivity to olefin oxide" is taken to mean the mole percent of reacted olefin which goes to form olefin oxide. The conversion and selectivity of the process of this invention can vary over a wide range. Such process variables as the temperature, pressure, flow rate, concentration of oxygen, and concentration of water influence the conversion and selectivity. Generally, as the concentration of oxygen in the feed stream increases, the conversion of olefin also increases, while the selectivity for olefin oxide decreases. Generally, as the temperature of the reaction increases, the conversion also increases, while the selectivity decreases. By adjusting the process parameters of the invention, the skilled artisan can obtain simultaneously an acceptable conversion and a high selectivity in the epoxidation of the higher olefins, like propylene. Typically, the catalyst of this invention produces an olefin conversion of at least about 0.1 percent. Preferably, the catalyst produces a conversion greater than about 0.2 percent; more preferably a conversion greater than about 0.6 percent; most preferably, greater than about 1.0 percent. Typically, the catalyst of this invention produces a selectivity to olefin oxide greater than about 20 percent. Preferably, the catalyst produces a selectivity to olefin oxide greater than about 28 percent; more preferably, a selectivity greater than about 40 percent; most preferably, greater than about 50 percent.

In addition to the conversion and selectivity, a convenient measure of the activity of the mixed silver-promoter silicate catalyst is the specific epoxidation rate. For the purposes of this invention, the term "specific epoxidation rate" is taken to mean the grams of olefin oxide formed per kilogram of silver per hour. Typically, the specific epoxidation rate is greater than about 0.8 gram of olefin oxide formed per kilogram of silver per hour. Preferably, the specific epoxidation rate is greater than about 3 grams of olefin oxide per kilogram of silver per hour; more preferably, greater than about 6 grams of olefin oxide per kilogram of silver per hour.

The invention is further illustrated by the following, non-limiting examples. All percentages are given as mole percent, unless otherwise noted.

EXAMPLE 1

A first solution is prepared containing $Na_2SiO_3 \cdot 9H_2O$ (37.2 g, 131 mmoles) in 1.5 liters of water. A second solution is prepared containing $AgNO_3$ (36.4 g, 214 mmoles) and $Mg(NO_3)_2 \cdot 6H_2O$ (5.3 g, 20.7 mmoles) in 1.5 liters of water. The first solution is added to the second solution at room temperature to form an orange precipitate. The resulting orange precipitate and mother liquor are heated at 95° C. for one hour. The mixture is cooled to room temperature and filtered. The filter cake is washed by breaking up the cake and suspending the particles in 2.0 liters of water. The suspended particles are refiltered. The filter cake is washed two or three more times in the same manner. The washed filter cake is dried by heating at 150° C. overnight. The dried cake is reduced at 125° C. overnight with a 10 percent hydrogen in nitrogen gas mixture. The reduced material is used as an oxidation catalyst for propylene, as described hereinabove, to obtain the results shown in Table I.

EXAMPLE 2

A solution containing predominately $Si_2O_5^{-2}$ is prepared by heating a solution of $Na_2SiO_3 \cdot 9H_2O$ (35.8 g, 126 mmoles) in 0.175 liter of water to boiling and then dropwise adding 7.6 ml of 16N $HNO_3$, allowing any precipitate to dissolve before adding the next drop of $HNO_3$. A second solution is prepared containing $AgNO_3$ (17.9 g, 106 mmoles) and $Mg(NO_3)_2 \cdot 6H_2O$ (2.66 g, 10.4 mmoles) in 2.0 liters of water. The second solution is heated to 90° C. The $Si_2O_5^{-2}$ solution is added to the heated second solution at a rate of 50 ml/minute to form an orange-yellow precipitate. This precipitate is heated with the mother liquor at 90° C. for 2 hours, then cooled to room temperature and filtered. The filtered solid is washed, dried, reduced at 100° C.-200° C. and used as a catalyst as in Example 1. The oxidation activity is shown in Table I.

EXAMPLE 3

A solution containing predominately $Si_3O_7^{-2}$ is prepared by heating a solution of $Na_2SiO_3 \cdot 9H_2O$ (58.5 g, 206 mmoles) in 0.20 liter of water to boiling, and then adding 16 ml of 16N $HNO_3$ in the same manner as described in Example 2. This solution is diluted with water to a total volume of 1.20 liters. A second solution is prepared containing $AgNO_3$ (20.7 g, 122 mmoles) and $Mg(NO_3)_2 \cdot 6H_2O$ (3.04 g, 119 mmoles) in 2.0 liters of water. The second solution is heated to 90° C. The diluted $Si_3O_7^{-2}$ solution is added to the heated second solution at a rate of 50 ml/minute to form a yellow precipitate. This precipitate is heated with the mother liquor at 90° C. for 2 hours, then cooled to room temperature and filtered. The filtered solid is washed, dried, reduced at 100° C.-200° C. and used as a catalyst as in Example 1, with the results given in Table I.

EXAMPLE 4

Cab-O-Sil®, M-5 brand fumed silica (20.39 g) is suspended in 1.75 liters of water containing dissolved $Na_2SiO_3 \cdot 9H_2O$ (8.81 g, 31 mmoles). The suspension is heated at 90° C. for one hour. A second solution is prepared containing $AgNO_3$ (8.70 g, 51.2 mmoles) and $Mg(NO_3)_2 \cdot 6H_2O$ (1.32 g, 5.2 mmoles) in 2.0 liters of water heated at 90° C. The Cab-O-Sil® suspension is added to the heated second solution to form a precipitate which is heated with the mother liquor at 95° C. for 2 hours, then cooled to room temperature and filtered. The filtered solid is washed, dried, reduced at 150° C. and used as described in Example 1. The results are given in Table I.

EXAMPLE 5

Cab-O-Sil® M-5 brand fumed silica (21.35 g) is suspended in 1.5 liters of water. In a separate flask a solution of $Na_2SiO_3 \cdot 9H_2O$ (17.7 g, 62.3 mmoles) in 0.10 liter of water is heated to boiling and 4 ml of 16N $HNO_3$ is added as described in Example 2. The heated solution is added to the suspension forming an enriched suspension. A second solution is prepared containing $AgNO_3$ (8.77 g, 51.9 mmoles) and $Mg(NO_3)_2 \cdot 6H_2O$ (1.35 g, 5.27 mmoles) in 2.0 liters of water. The enriched suspension is added to the second solution at 90° C. to produce an orange precipitate which is heated with the mother liquor at 90° C. for 90 minutes. Afterwards the precipitate is cooled to room temperature, filtered, washed, dried, reduced at 150° C. and used as described in Example 1. The results are found in Table I.

EXAMPLE 6

A first solution is prepared by dissolving $Na_2SiO_3.9H_2O$ (51.68 g, 182 mmoles) in 200 ml of water, adding 11.4 ml of concentrated $HNO_3$, and diluting with water to a total volume of 2.0 liters. A second solution of $AgNO_3$ (25.59 g, 151 mmoles) and $Eu(NO_3)_3.6H_2O$ (4.73 g, 10.6 mmoles) in 2.0 liters of water is added to the first solution. A precipitate forms and is heated for two hours at 90° C. in the presence of the mother liquor. The precipitate is filtered, washed, dried, reduced and used as described in Example 1 with the results shown in Table I.

EXAMPLE 7

A first solution of $Na_2SiO_3.9H_2O$ (38.7 g, 136 mmoles) in 1.60 liters of water is added to a second solution of $AgNO_3$ (36.7 g, 216 mmoles) and $Ca(NO_3)_2.4H_2O$ (5.01 g, 21.2 mmoles) in 1.50 liters of water. The resulting precipitate is washed, dried, reduced and used as described in Example 1 with results shown in Table I.

EXAMPLE 8

A first solution is prepared by dissolving $Na_2SiO_3.9H_2O$ (51.66 g, 182 mmoles) in 200 ml of water, heating to boiling, adding 11.5 cc of concentrated $HNO_3$, and diluting with water to a total volume of 2.0 liters. A second solution is prepared containing $AgNO_3$ (25.51 g, 150 mmoles) and $Lu(NO_3)_3.17.4$ percent $H_2O$ (4.41 g, 8.43 mmoles) in 2.0 liters of water. The first solution is added to the second solution, and the resulting precipitate is heated at 90° C. for two hours. The precipitate is washed, dried, reduced and used as described in Example 1 with results shown in Table I.

EXAMPLE 9

A first solution of $Na_2SiO_3.9H_2O$ (37.1 g, 131 mmoles) in 1.5 liters of water is added to a second solution of $AgNO_3$ (36.1 g, 213 mmoles) and $Cd(NO_3)_2.4H_2O$ (6.55 g, 21.2 mmoles) in 1.5 liters of water. The resulting precipitate is washed, dried, reduced and used as described in Example 1 with results shown in Table I.

EXAMPLE 10

A first solution of $Na_2SiO_3.9H_2O$ (38.2 g, 134 mmoles) in 1.5 liters of water is added to a second solution of $AgNO_3$ (36.6 g, 216 mmoles) and $Cu(NO_3)_2.\frac{1}{2}H_2O$ (5.03 g, 21.6 mmoles) in 1.5 liters of water. The resulting precipitate is washed, dried, reduced and used as described in Example 1 with results shown in Table I.

EXAMPLE 11

A first solution of $Na_2SiO_3.9H_2O$ (38.9 g, 137 mmoles) in 1.5 liters of water is added to a second solution of $AgNO_3$ (36.3 g, 214 mmoles) and $Ni(NO_3)_2.6H_2O$ (6.46 g, 22.2 mmoles) in 1.5 liters of water. The resulting precipitate is washed, dried, reduced and used as described in Example 1 with results shown in Table I.

EXAMPLE 12

A first solution of $Na_2SiO_3.9H_2O$ (38.9 g, 137 mmoles) in 1.5 liters of water is added to a second solution of $AgNO_3$ (36.5 g, 215 mmoles) and $Co(NO_3)_2.6H_2O$ (6.25 g, 21.5 mmoles) in 1.5 liters of water. The resulting precipitate is washed, dried, reduced and used as described in Example 1 with results shown in Table I.

EXAMPLE 13

A first solution is prepared by dissolving $Na_2SiO_3.9H_2O$ (52.24 g, 184 mmoles) in 200 ml of water, heating to boiling, adding slowly 11.5 cc of concentrated $HNO_3$, and diluting with water to a total volume of 2.0 liters. A second solution is prepared by dissolving $AgNO_3$ (25.68 g, 151 mmoles) and $Pr(NO_3)_3H_2O$ (4.43 g, 13 mmoles) in 2.0 liters of water at 90° C. The first solution is added to the second solution, and the resulting precipitate and mother liquor are heated at 90° C. for two hours. The resulting precipitate is washed, dried, reduced at 150° C., and used as described in Example 1 with results shown in Table I.

EXAMPLE 14

A first solution of $Na_2SiO_3.9H_2O$ (39.8 g, 141 mmoles) in 1.5 liters of water is added to a second solution of $AgNO_3$ (36.3 g, 214 mmoles), $Ca(NO_3)_2.4H_2O$ (2.51 g, 10.9 mmoles), and $Zn(NO_3)_2.6H_2O$ (3.19 g, 10.7 mmoles) in 1.5 liters of water. The resulting precipitate is washed dried, reduced and used as described in Example 1 with results shown in Table I.

EXAMPLE 15

A first solution of $Na_2SiO_3.9H_2O$ (40.0 g, 141 mmoles) in 1.5 liters of water is added to a second solution of $AgNO_3$ (37.4 g, 221 mmoles), $Ca(NO_3)_2.4H_2O$ (2.58 g, 10.9 mmoles), and $Cd(NO_3)_2.4H_2O$ (3.36 g, 10.9 mmoles) in 1.5 liters of water. The resulting precipitate is washed, dried, reduced and used as described in Example 1 with results shown in Table I.

EXAMPLE 16

A first solution of $Na_2SiO_3.9H_2O$ (56.5 g, 199 mmoles) in 1.2 liters of water at 90° C. is added to a second solution at 90° C., prepared as follows:. A solution of $Bi(NO_3)_3.5H_2O$ (4.51 g, 9.30 mmoles) in 5 ml of 16N $HNO_3$ is diluted with several ml of water. $AgNO_3$ (39.9 g, 235 mmoles) and $Mg(NO_3)_2.6H_2O$ (5.99 g, 23.4 mmoles) are added to the diluted $Bi(NO_3)_3$ solution, the resulting mixture is further diluted with water to 1.5 liters volume. The resulting precipitate is heated with the mother liquor for 2 hours at 90° C.; then cooled, washed, dried, reduced and used as described in Example 1 with the results shown in Table I.

TABLE I

| Example No. | Catalyst wt (g) | Oxidation of Propylene* | | | | |
| --- | --- | --- | --- | --- | --- | --- |
| | | Temp (°C.) | Flow, cc/min | % Conversion | % Selectivity | SER* |
| 1 | 14.2 | 180 | 10 | 12.3 | 16.8 | 2.6 |
| | | 140 | 10 | 1.74 | 49.7 | 1.1 |
| | | 121 | 10 | 0.40 | 57.0 | 2.8 |
| | | 138 | 10 | 1.35 | 54.6 | 0.92 |
| 2 | 12.3 | 180 | 50 | 3.73 | 47.2 | 16.0 |
| | | 150 | 50 | 0.85 | 60.8 | 4.7 |
| | | 120 | 20 | 0.27 | 63.2 | 0.62 |
| | | 155 | 50 | 1.13 | 60.2 | 6.2 |
| | | 165 | 50 | 3.63 | 42.9 | 13.9 |
| 3 | 15.0 | 145 | 50 | 1.33 | 53.9 | 6.4 |
| | | 115 | 20 | 0.46 | 57.4 | 0.95 |
| | | 140 | 50 | 1.07 | 55.6 | 5.3 |
| 4 | 11.3 | 180 | 20 | 2.84 | 25.6 | 7.95 |
| | | 150 | 10 | 0.88 | 37.6 | 1.8 |

TABLE I-continued

Oxidation of Propylene*

| Example No. | Catalyst wt (g) | Temp (°C.) | Flow, cc/min | % Conversion | % Selectivity | SER* |
|---|---|---|---|---|---|---|
|   |   | 135 | 10 | 0.40 | 39.7 | 0.87 |
|   |   | 190 | 60 | 2.38 | 33.7 | 34.8 |
| 5 | 9.4 | 160 | 60 | 0.40 | 54.6 | 9.5 |
|   |   | 190 | 150 | 0.95 | 41.4 | 42.7 |
| 6 | 10.0 | 150 | 100 | 0.40 | 59.6 | 5.22 |
|   |   | 170 | 100 | 1.49 | 50.6 | 16.6 |
| 7 | 7.0 | 165 | 10 | 1.15 | 33.3 | 0.93 |
| 8 | 10.0 | 120 | 100 | 0.54 | 31.5 | 4.0 |
| 9 | 7.0 | 150 | 10 | 1.32 | 38.0 | 1.2 |
| 10 | 7.0 | 140 | 10 | 0.83 | 36.6 | 0.73 |
| 11 | 7.0 | 150 | 10 | 1.45 | 39.2 | 1.37 |
| 12 | 7.0 | 150 | 10 | 1.78 | 28.4 | 1.22 |
| 13 | 10.0 | 150 | 100 | 0.33 | 58.4 | 4.2 |
|   |   | 170 | 100 | 1.01 | 54.5 | 12.0 |
| 14 | 15.0 | 145 | 20 | 1.25 | 44.3 | 2.7 |
| 15 | 15.0 | 135 | 10 | 1.28 | 47.1 | 1.5 |
| 16 | 15.0 | 130 | 10 | 1.41 | 50.4 | 1.7 |

*Feedstream: About 70% (vol) propylene and about 30% (vol) oxygen premixed, then saturated with $H_2O$ at about 25° C. to about 3% (vol) $H_2O$ vapor. Pressure, about 14.6 psia. SER = g propylene oxide $kg^{-1}$ Ag $hr^{-1}$.

The data in Table I show the activity of the the catalysts prepared in Examples 1–16 in the oxidation of propylene. It is seen that the process conditions for the oxidation reaction are quite mild. A wide range of conversions is observed from a low of 0.4 mole percent to a high of 12.3 mole percent. Generally, the selectivity to propylene oxide is observed to be high. The lowest of such observed selectivities is 16.8 mole percent, while the highest is 63.2 mole percent. The selective epoxidation rate is found to be surprisingly good, ranging from a low of 0.62 g propylene oxide per kg silver per hour to a high of 42.7 g propylene oxide per kg silver per hour.

EXAMPLE 17

A first solution comprising $Si_2O_5^{-2}$ is prepared by adding 19.0 ml of concentrated (16M) nitric acid with stirring to a solution of $NaSiO_3 \cdot 9H_2O$ (91.30 g; 350 mmoles) in 200 ml of boiling water. In a separate flask Cab-O-Sil ® M-5 Fumed Silica (106.38 g; Cabot Corp.) is suspended in 2.0 liters of water at 90° C. The $Si_2O_5^{-2}$ solution is added to the suspension of Fumed Silica, and the resulting $Si_2O_5^{-2}$/Fumed Silica mixture is heated at 90° C. with stirring. $AgNO_3$ (42.04 g; 250 mmoles) and $Mg(NO_3)_2 \cdot 6H_2O$ (9.52 g; 37 mmoles) are heated with stirring in 2.0 liters of water at 90° C. to make a second solution. The $Si_2O_5^{-2}$/Fumed Silica mixture is then added to the second solution at the rate of 60 cc/minute. The resulting mixture is heated at 90° C. for 2 hours. The mixture is cooled overnight. The precipitate is filtered; and then resuspended in 2.0 liters of water and refiltered. The resuspension and refiltration are repeated three times. The resulting filtercake is dried in air overnight at 150° C. The dried filtercake is reduced in 5 percent hydrogen in nitrogen; the reduction commencing at room temperature and continuing at a rate of 5° C./minute to 200° C., where the reduction is maintained for two hours. The solid is cooled to room temperature under the hydrogen and nitrogen stream to yield a mixed silver-magnesium silicate catalyst. The catalyst is used in the epoxidation of propylene with the results given in Table II.

TABLE II*

| Ex. 17 | Pressure (psia) | Temp (°C.) | Flow (cc/min) | % $O_2$ (vol) | % $H_2O$ (vol) | % Conversion | % Selectivity | SER |
|---|---|---|---|---|---|---|---|---|
| (a) | 14.6 | 130 | 70 | 25.6 | 3 | 0.27 | 48.8 | 6.0 |
| (b) | 14.6 | 140 | 60 | 10.5 | 3 | 0.11 | 59.9 | 3.2 |
| (c) | 14.6 | 140 | 70 | 25.2 | 3 | 0.53 | 44.7 | 10.8 |
| (d) | 14.6 | 160 | 70 | 13.4 | 3 | 1.16 | 22.2 | 13.8 |
| (e) | 53 | 170 | 2000 | 23.4 | 0.1 | 0.26 | 54.3 | 26.5 |
| (f) | 53 | 170 | 2000 | 22.7 | 0.5 (70° C.) | 0.26 | 63.8 | 31.1 |
| (g) | 53 | 170 | 720 | 22.3 | 0.1 | 0.38 | 68.1 | 48.6 |
| (h) | 63 | 170 | 720 | 21.9 | 0.3 (37° C.) | 0.42 | 72.6 | 58.6 |
| (i) | 75 | 170 | 1100 | 10.9 | 0.1 | 0.39 | 73.8 | 97.4 |
| (j) | 75 | 185 | 1100 | 11.0 | 0.1 | 0.24 | 51.0 | 41.8 |

*Feed: Propylene and oxygen are premixed in the indicated volume %, then bubbled through $H_2O$ at 25° C., unless noted otherwise, to the indicated % (vol) $H_2O$ vapor. Catalyst: a–d, 10.0 g; e–i, 25.0 g. SER = g propylene oxide per kg Ag per hour.

The data in Table II indicate the trends and ranges in conversion, selectivity, and selective epoxidation rate which are obtained on varying the process parameters. For example, it is seen that as the pressure increases (17 g vs. 17 h), the conversion of propylene and selectivity for propylene oxide increase. The conversion of propylene is seen to range from a low of 0.11 mole percent to a high of 1.16 mole percent. The selectivity to propylene oxide is seen to range from a low of 22.2 mole percent to a high of 73.8 mole percent. The selective epoxidation rate is seen to range from a low of 3.2 g propylene oxide per kg Ag per hr to a high of 97.4 g propylene oxide per kg Ag per hr.

EXAMPLE 18

A catalyst is prepared as described in Example 2. The catalyst is used in the epoxidation of propylene with the results shown in Table III.

TABLE III*

| Ex. 18 | % $O_2$ (vol) | % $H_2O$ (vol) | T $H_2O$ Bath, (°C.) | % Conversion | % Selectivity | SER |
|---|---|---|---|---|---|---|
| (a) | 33 | 3.1 | 25 | 0.88 | 52.0 | 6.8 |
| (b) | 33 | 5.5 | 35 | 1.83 | 47.0 | 12.9 |
| (c) | 33 | 9.3 | 45 | 2.25 | 36.6 | 12.3 |
| (d) | 19 | 0.6 | 0 | 0.27 | 52.3 | 2.6 |
| (e) | 19 | 4.2 | 30 | 0.33 | 55.1 | 3.3 |
| (f) | 19 | 7.30 | 40 | 0.42 | 50.2 | 3.8 |
| (g) | 19 | 12.2 | 50 | 0.66 | 42.2 | 5.0 |

*Feed Propylene and oxygen are premixed in the indicated % (vol), then bubbled through water at 25° C. to the indicated % (vol) water vapor. Catalyst: 25.0 g; Pressure: 14.6 psia; T: 155° C.; Flow rate: 50 cc/min. SER = g propylene oxide per kg Ag per hour.

The data in Table III indicate the trends and ranges in conversion, selectivity, and selective epoxidation rate which are obtained on varying the oxygen and water concentrations. As the concentration of water increases (18a–c, d–g), the conversion increases, while the selectivity for propylene oxide typically decreases. As the concentration of oxygen increases (18a vs 18e), the conversion increases. The conversion of propylene is seen to range from a low of 0.27 mole percent to a high of 2.25 mole percent. The selectivity to propylene oxide is seen to range from a low of 36.6 mole percent to a high of 55.1 mole percent. The selective epoxidation rate is seen to range from a low of 2.6 g propylene oxide per kg Ag per hr to a high of 12.9 g propylene oxide per kg Ag per hr.

What is claimed is:

1. The invention is the process of epoxidizing higher olefins comprising contacting at least one higher olefin with oxygen in the presence of a catalyst under conditions sufficient to produce the corresponding olefin oxide; the catalyst being prepared by a process comprising contacting in an aqueous solution the following dissolved salts;
   (a) a silver-containing salt;
   (b) at least one salt containing a multivalent cation promoter: and
   (c) a silicon-containing salt, wherein the mole ratio of silicon to combined silver and promoter metals is at least about 0.5,
under conditions sufficient to form a mixed silver-promoter silicate precipitate which when tested as a catalyst in the epoxidation of propylene produces a conversion of propylene greater than about 0.2 mole percent and a selectivity to propylene oxide greater than about 28 mole percent.

2. The process of claim 1 wherein the mole ratio of silver to combined promoter metals is greater than about 1.4:1 and less than about 100:1.

3. The process of claim 1 in which the silver salt is silver nitrate.

4. The process of claim 1 wherein the silicate-containing salt is a Group IA metal silicate.

5. The process of claim 4 in which the silicate salt is sodium silicate.

6. The process of claim 1 in which the promoter salt is a water-soluble nitrate having a dipositive or tripositive cation selected from the group of metals consisting of berylium, magnesium, calcium, strontium, barium, cobalt, nickel, copper, zinc, cadmium, praseodymium, neodymium, europium, gadolinium, holmium and lutetium or mixtures thereof.

7. The process of claim 6 wherein the promoter metal is magnesium.

8. The process of claim 6 wherein the promoter metal is praeseodymium.

9. The process of claim 6 wherein the promoter metal is europium.

10. The process of claim 1 in which the higher olefin is propylene.

11. The process of claim 1 wherein the oxygen to olefin mole ratio is above about 0.05:1 and below about 0.40:1.

12. The process of claim 1 in which the temperature is above about 100° C. and below about 250° C.

13. The process of claim 1 wherein the pressure is in the range from about 7 psia to about 300 psia.

14. The process of claim 1 wherein the space velocity is in the range from about 10 $hr^{-1}$ to about 6000 $hr^{-}$.

15. The process of claim 1 wherein the conversion of olefin is greater than about 0.6 mole percent and the selectivity to olefin oxide is greater than about 40 mole percent.

16. The process of claim 1 wherein the conversion of olefin is greater than about 1.0 mole percent and the selectivity to olefin oxide is greater than about 50 mole percent.

17. The process of claim 1 wherein the specific epoxidation rate is greater than about 0.8 gram of olefin oxide formed per kilogram of silver per hour.

18. The process of claim 1 wherein the specific epoxidation rate is greater than about 3 grams of olefin oxide formed per kilogram of silver per hour.

19. The process of claim 1 wherein the catalyst is supported on an inert carrier.

20. The process of claim 19 wherein the catalyst is supported on fumed silica.

* * * * *